(12) United States Patent
Kabaya et al.

(10) Patent No.: US 8,142,429 B2
(45) Date of Patent: Mar. 27, 2012

(54) HIGH-FREQUENCY TREATMENT BASED UPON A CALCULATED IMPEDANCE

(75) Inventors: Akinori Kabaya, Hachioji (JP); Takashi Mihori, Akiruno (JP)

(73) Assignee: Olympus Medical Systems Corp. (JP)

( * ) Notice: Subject to any disclaimer, the term of this patent is extended or adjusted under 35 U.S.C. 154(b) by 742 days.

(21) Appl. No.: 12/244,920

(22) Filed: Oct. 3, 2008

(65) Prior Publication Data

US 2010/0087894 A1  Apr. 8, 2010

(51) Int. Cl.
*A61B 18/18* (2006.01)
(52) U.S. Cl. .................................. 606/42; 606/48
(58) Field of Classification Search .............. 606/32, 606/33, 48–52, 62, 42
See application file for complete search history.

(56) References Cited

U.S. PATENT DOCUMENTS 7,901,400 B2 * 3/2011 Wham et al. .................. 606/34

FOREIGN PATENT DOCUMENTS

| JP | 2000-107197 | 4/2000 |
|---|---|---|
| JP | 2001-29355 | 2/2001 |
| JP | 2001-252284 | 9/2001 |
| JP | 2001-269353 | 10/2001 |

\* cited by examiner

*Primary Examiner* — Kevin C Sirmons
*Assistant Examiner* — Bradley Osinski
(74) *Attorney, Agent, or Firm* — Ostrolenk Faber LLP

(57) ABSTRACT

A high-frequency treatment apparatus includes a treatment high-frequency wave output unit configured to output a treatment high-frequency wave to be applied to a treatment target living tissue, a detection unit for detecting an impedance of the treatment target living tissue, and a control unit configured to control the treatment high-frequency wave output unit on the basis of the result of the detection in the detection unit, the control unit configured to set a treatment frequency of the treatment high-frequency wave to a first treatment frequency in order to treat the living tissue primarily by Joule heat when the impedance of the treatment target living tissue is lower than a threshold value and to set the treatment frequency to a second treatment frequency higher than the first treatment frequency in order to treat the living tissue primarily by high-frequency dielectric heating when the impedance of the treatment target living tissue is higher than the threshold value.

13 Claims, 7 Drawing Sheets

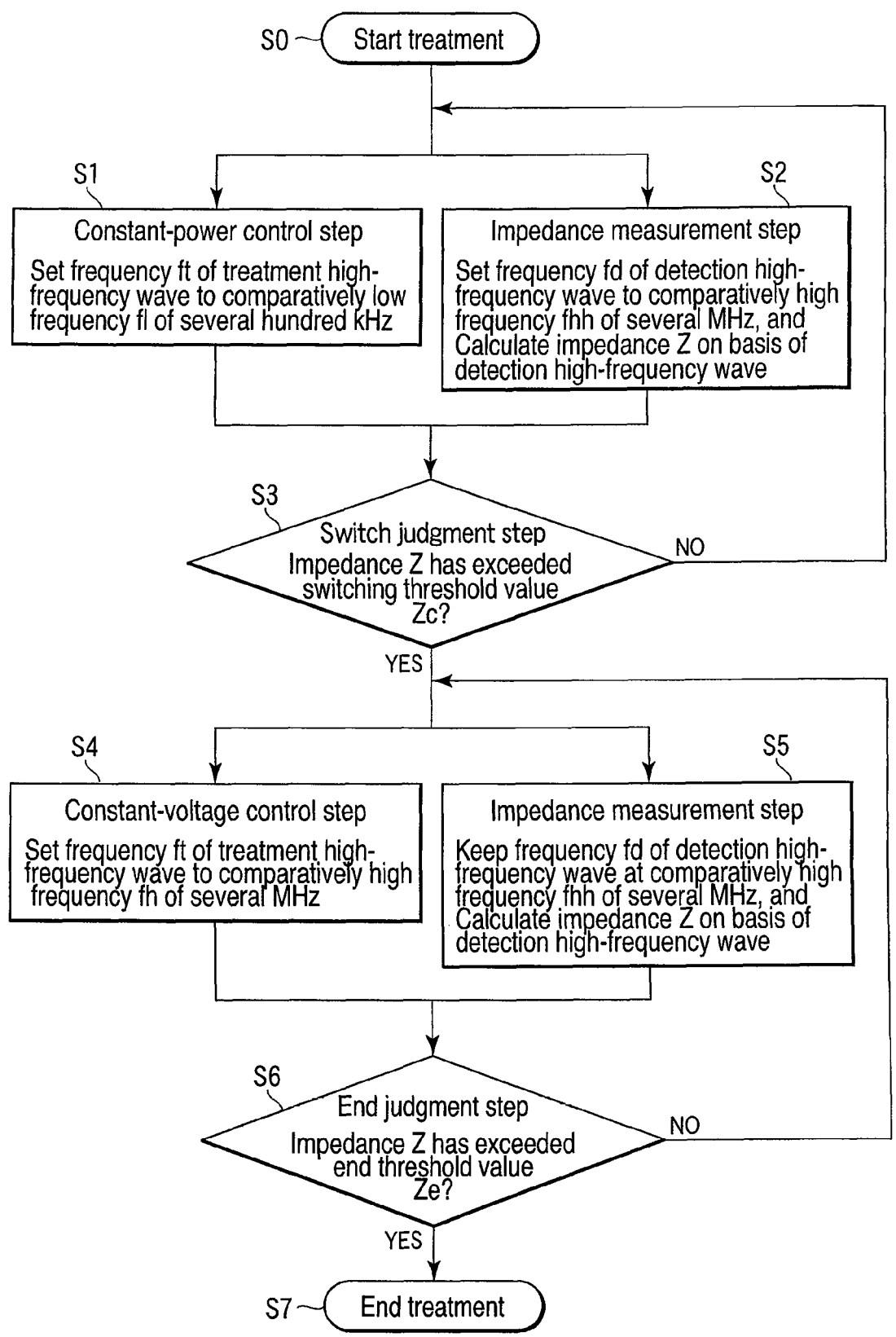
F I G. 11

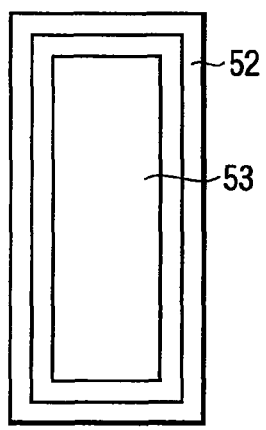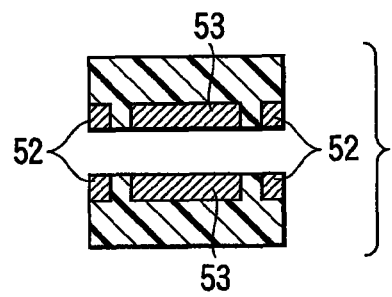
FIG. 15A  FIG. 15B
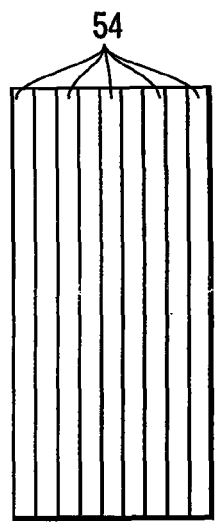
FIG. 16
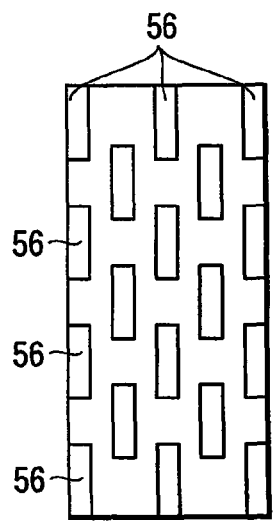
FIG. 17

HIGH-FREQUENCY TREATMENT BASED UPON A CALCULATED IMPEDANCE

BACKGROUND OF THE INVENTION

1. Field of the Invention

The present invention relates to a high-frequency treatment apparatus and a high-frequency treatment method for applying a treatment high-frequency wave to a living tissue to treat the living tissue.

2. Description of the Related Art

In a high-frequency treatment apparatus, for example, a pair of electrodes holds a living tissue and a high-frequency wave is applied to the held living tissue, and so the living tissue is treated. In such a high-frequency treatment apparatus, an impedance of the held living tissue is measured, and the current value, voltage value, power value, frequency, etc. of the high-frequency wave to be applied to the living tissue is controlled on the basis of the measured impedance so as to perform a suitable treatment. Various kinds of control methods for performing a suitable coagulation/incision treatment are disclosed in, for example, Jpn. Pat. Appln. KOKAI Publication No. 2001-269353, Jpn. Pat. Appln. KOKAI Publication No. 2001-29355, Jpn. Pat. Appln. KOKAI Publication No. 2000-107197 and Jpn. Pat. Appln. KOKAI Publication No. 2001-252284.

BRIEF SUMMARY OF THE INVENTION

In an aspect of the present invention, a high-frequency treatment apparatus includes: a treatment high-frequency wave output unit configured to output a treatment high-frequency wave to be applied to a treatment target living tissue; a detection unit for detecting an impedance of the treatment target living tissue; and a control unit configured to control the treatment high-frequency wave output unit on the basis of the result of the detection in the detection unit, the control unit configured to set a treatment frequency of the treatment high-frequency wave to a first treatment frequency in order to treat the living tissue primarily by Joule heat when the impedance of the treatment target living tissue is lower than a threshold value and to set the treatment frequency to a second treatment frequency higher than the first treatment frequency in order to treat the living tissue primarily by high-frequency dielectric heating when the impedance of the treatment target living tissue is higher than the threshold value.

In another aspect of the present invention, a high-frequency treatment method includes: detecting an impedance of a treatment target living tissue; performing a first treatment wherein a treatment high-frequency wave of a first treatment frequency is applied to the living tissue in order to treat the living tissue primarily by Joule heat when the impedance of the treatment target living tissue is lower than a threshold value; and performing a second treatment wherein a treatment high-frequency wave of a second treatment frequency higher than the first treatment frequency is applied to the living tissue in order to treat the living tissue primarily by high-frequency dielectric heating when the impedance of the treatment target living tissue is higher than the threshold value.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 11 is a flowchart showing a high-frequency treatment method according to the second embodiment of the present invention;

FIG. 15A is a front view showing electrodes according to a first reference embodiment of the present invention;

FIG. 15B is a transverse cross-sectional view showing the electrodes according to the first reference embodiment of the present invention;

FIG. 16 is a front view showing electrodes according to a second reference embodiment of the present invention; and FIG. 17 is a front view showing electrodes according to a third reference embodiment of the present invention.

DETAILED DESCRIPTION OF THE INVENTION

Embodiments of the present invention will be described with reference to the drawings.

A high-frequency treatment apparatus and a high-frequency treatment method used in a treatment for coapting living tissues such as a digestive tract are described below by way of example.

A first embodiment of the present invention is described with reference to FIGS. 1 to 8.

Figure 1:
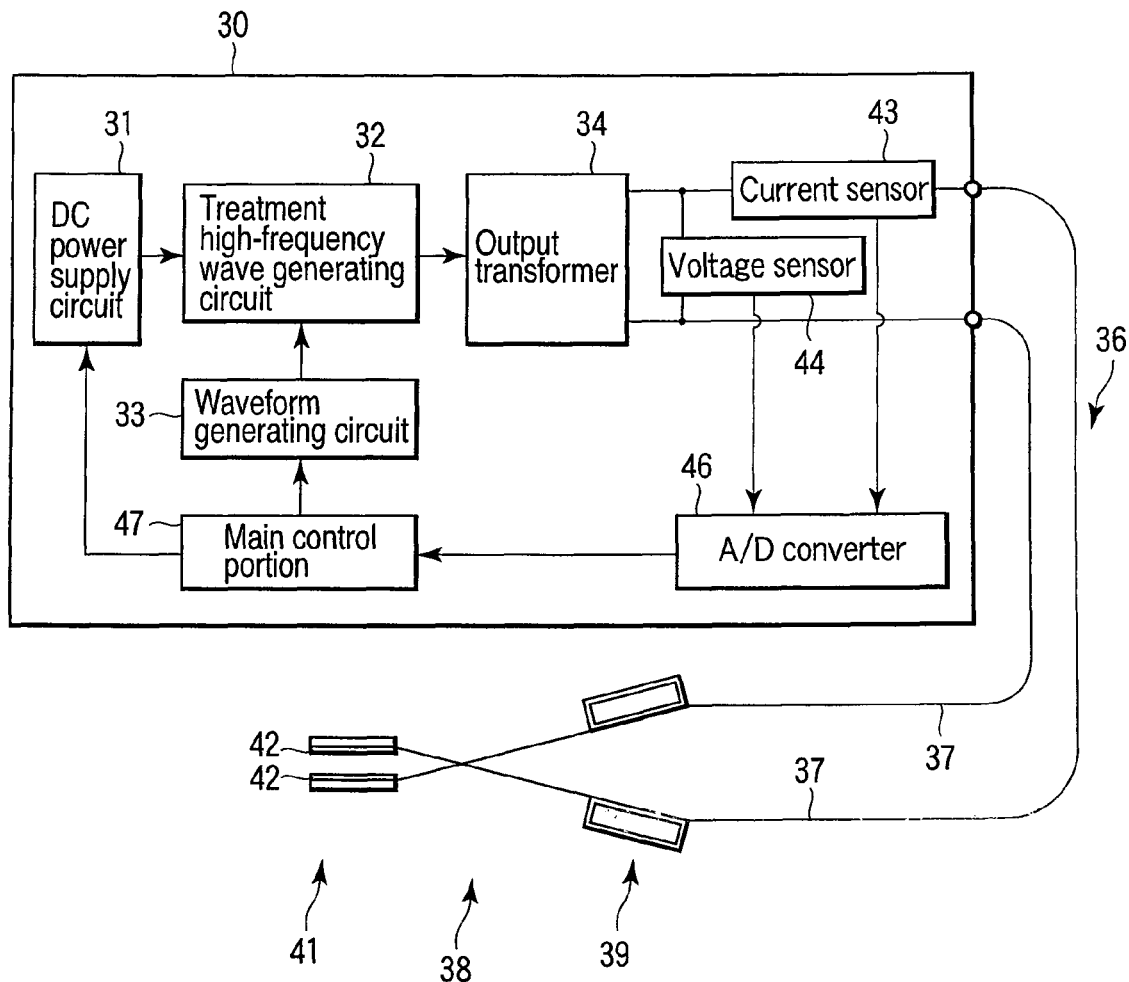
FIG. 1 is a block diagram showing a high-frequency treatment apparatus according to a first embodiment of the present invention.

The high-frequency treatment apparatus is described with reference to FIG. 1.

In a high-frequency treatment system, a treatment high-frequency wave for treating a living tissue is used. That is, in a power supply apparatus 30, a DC power supply circuit 31 is configured to supply power to a treatment high-frequency wave generating circuit 32. The treatment high-frequency wave generating circuit 32 is configured to generate a treatment high-frequency wave under the control of a waveform generating circuit 33, and to output the treatment high-frequency wave to an output transformer 34. The output transformer 34 is connected to a pair of output terminals. The pair of output terminals of the power supply apparatus 30 is connected to a pair of signal lines 37 of a cable 36, respectively, and the pair of signal lines 37 of the cable 36 is connected to a pair of electrodes 42 of a high-frequency accessory 38, respectively. In the present embodiment, the high-frequency accessory 38 has a form of a forceps. That is, in the high-frequency accessory 38, a pair of jaws 41 on a distal side is configured to be opened and closed by opening and closing a pair of handles 39 on a proximal side, and the electrodes 42 are provided on closing direction sides in the pair of jaws 41, and the living tissue can be held by the pair of electrodes 42. When the living tissue is held by the pair of electrodes 42, the treatment high-frequency wave is supplied from the output transformer 34 of the power supply apparatus 30 to the pair of electrodes 42 of the high-frequency accessory 38 via the pair of signal lines 37 of the cable 36, and then the treatment high-frequency wave is applied to the held living tissue from the pair of electrodes 42, the living tissue is treated. In this way, a treatment high-frequency wave output unit is formed by the DC power supply circuit 31, the treatment high-frequency wave generating circuit 32 and the output transformer 34. Further, a current sensor 43 and a voltage sensor 44 for detecting current and voltage values of the high-frequency wave output from the output transformer 34 are arranged between the output transformer 34 and the output terminals. An A/D converter 46 is configured to A/D-convert the current and voltage values detected by the current sensor 43 and the voltage sensor 44, and to output them to a main control portion 47. The main control portion 47 is configured to calculate an impedance of the living tissue from the input current and voltage values, and to control the DC power supply circuit 31 and the waveform generating circuit 33 on the basis of the calculated impedance. In this way, a detection unit is formed by the current sensor 43, the voltage sensor 44, the A/D converter 46 and the main control portion 47, and a control unit is formed by the main control portion 47 and the waveform generating circuit 33.

The high-frequency treatment method is described with reference to FIGS. 2 to 8.

The chemical properties of the living tissue coaptation treatment are described.

It is considered that the coaptation of living tissues is formed by hydrogen bonding between polar groups of the tissues to be coapted, and is similar to an adhesive agent in principle. That is, protein of a living tissue is formed by peptide-bonded chains of amino acids of many kinds, polar groups such as NH and OH are contained in each of the peptide-bonded chains, and a three-dimensional structure peculiar to protein is formed by the regular hydrogen bonding of the polar groups. When energy such as heat is applied to the protein, protein denaturation is caused, and the hydrogen bonding between the polar groups is dissociated. Then, the dissociated polar groups are re-bonded between the living tissues to be coapted together, thereby coapting the living tissues together. Here, a water molecule is prone to be bonded to the polar group of protein, and when water molecular remain in the living tissue, the water molecule is bonded to the dissociated polar group, which inhibits the hydrogen bonding of the polar groups between the living tissues to be coapted together. That is, in order to coapting the living tissues surely, it is necessary to sufficiently dehydrate the living tissues and remove the water molecular from the living tissues.

Figure 2:
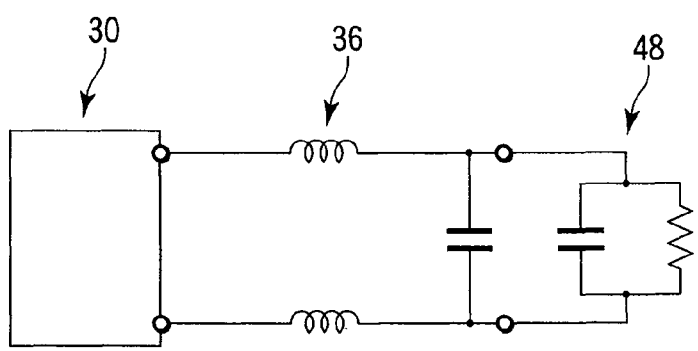
FIG. 2 is a schematic view showing a circuit model of a cable and a living tissue according to the first embodiment of the present invention.
Figure 3:
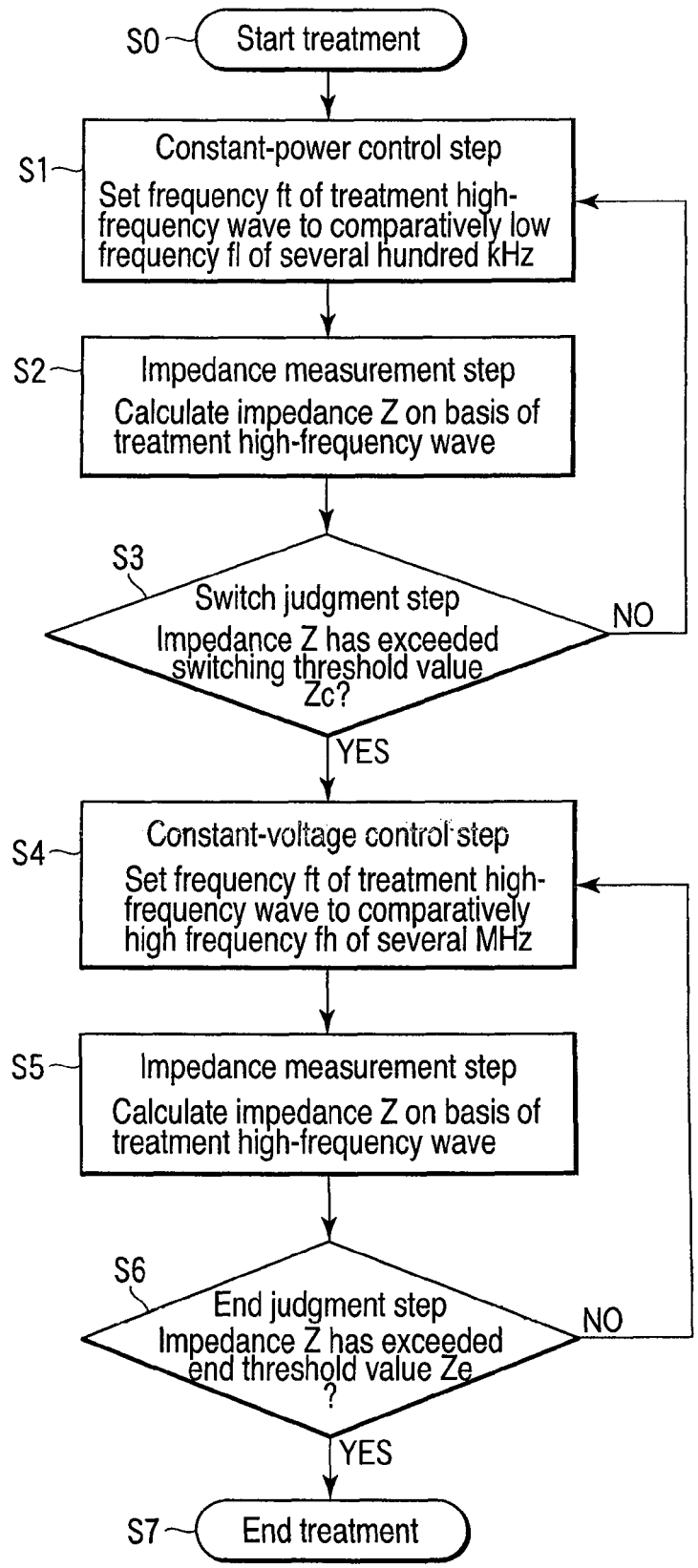
FIG. 3 is a flowchart showing a high-frequency treatment method according to the first embodiment of the present invention.
Figure 4:
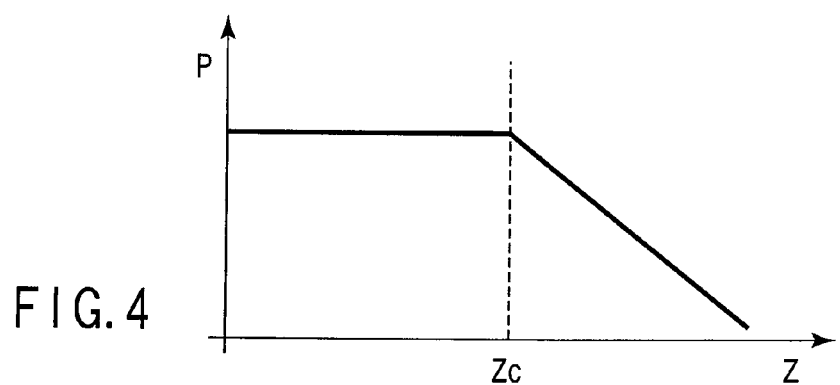
FIG. 4 is a graph showing the change of output power with respect to an impedance in the high-frequency treatment method according to the first embodiment of the present invention.
Figure 5:
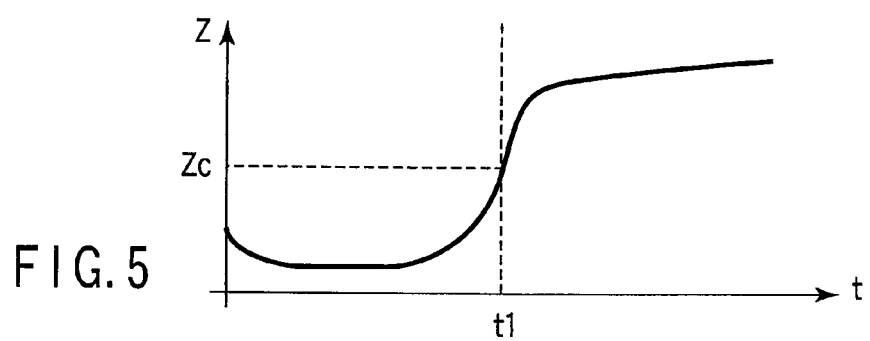
FIG. 5 is a graph showing the change of an impedance with respect to time in the high-frequency treatment method according to the first embodiment of the present invention.
Figure 6:
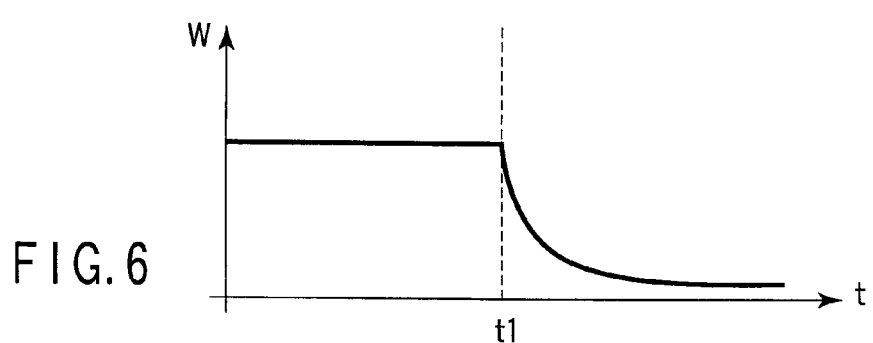
FIG. 6 is a graph showing the change of output power with respect to time in the high-frequency treatment method according to the first embodiment of the present invention.
Figure 7:
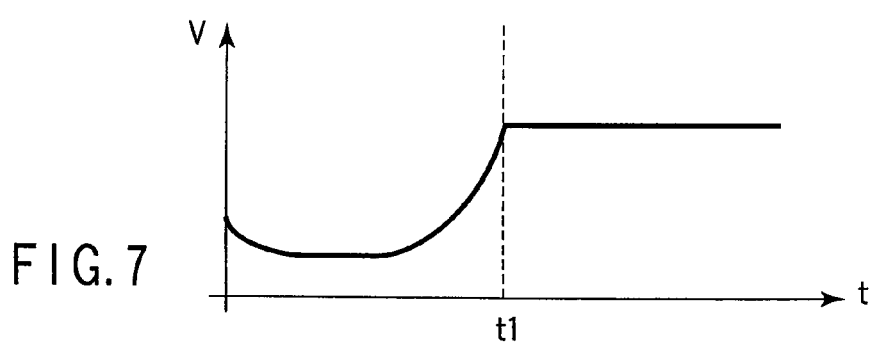
FIG. 7 is a graph showing the change of an output voltage with respect to time in the high-frequency treatment method according to the first embodiment of the present invention.
Figure 8:
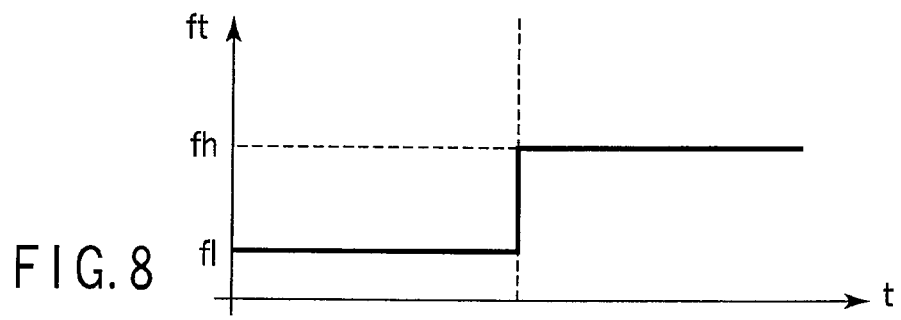
FIG. 8 is a graph showing the change of frequency with respect to time in the high-frequency treatment method according to the first embodiment of the present invention.
Figure 9:
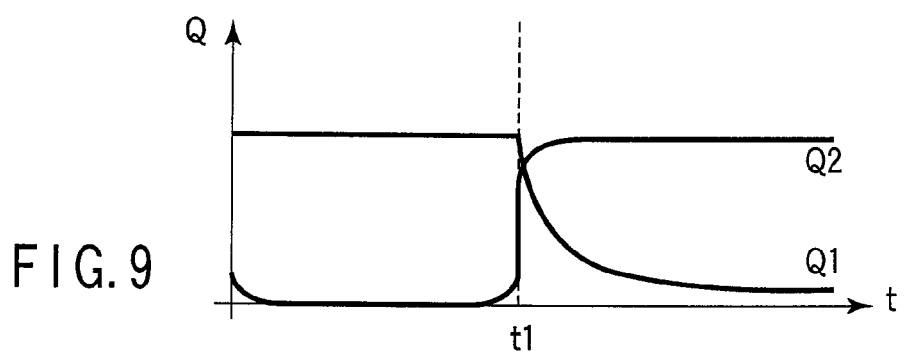
FIG. 9 is a graph showing the changes of calorific values derived from Joule heat and high-frequency dielectric heating with respect to time in the high-frequency treatment method according to the first embodiment of the present invention.

The electric properties of a living tissue 48 and the cable 36 are described with reference to FIG. 2.

It is possible to express the living tissue 48 as a parallel circuit of a resistor and a condenser. Regarding a cell of the living tissue 48, an extracellular fluid and an intracellular fluid have high conductivity and constitute a resistance component of the living tissue 48. On the other hand, a cell membrane has insulating properties and constitutes a capacity component of the living tissue 48. An impedance based on the capacity component is schematically in inverse proportion to the frequency of a high-frequency wave. The impedance of the living tissue 48 is changed by applying energy to the living tissue 48. That is, first, the impedance decreases when the cell membrane is broken. Then, the extracellular fluid and the intracellular fluid are increased in temperature, and the movement of ions in the extracellular fluid and the intracellular fluid is thus activated, such that the impedance moderately decreases. Then, the extracellular fluid and the intracellular fluid are further increased in temperature, and the evaporation of the extracellular fluid and the intracellular fluid is thereby started, such that the impedance moderately increases. Subsequently, the extracellular fluid and the intracellular fluid are boiled and evaporated, and a vapor layer is generated in the living tissue. The vapor layer has insulating properties, constitutes a capacity component and has a high impedance, so that the impedance of the living tissue rapidly increases. A value of the impedance to determine that the generation of the vapor layer in the living tissue has been stated is predetermined, and this value is a switching threshold value Zc. Energy is further applied to the living tissue 48 so that the remaining water molecular is sequentially boiled and evaporated, and the impedance moderately increases and comes closer to a fixed value. A value of the impedance to determine that the living tissue has been dehydrated completely is predetermined, and this value is an end threshold value Ze.

It is possible to express cable 36 as a coil in series with the living tissue 48 and a condenser in parallel therewith. Each of the signal lines 37 of the cable 36 has a predetermined induction coefficient, and constitutes an inductance component of the impedance of the cable 36. An impedance based on the capacity component is schematically in proportion to the frequency. Here, the cable 36 is comparatively long and has an overall length of, for example, about 3 m, and the influence of the inductance component is greater particularly when the frequency is high. Moreover, both the signal lines 37 form a condenser, and constitute a capacity component. An impedance based on the capacity component is schematically in inverse proportion to the frequency.

The high-frequency treatment method is described with reference to FIGS. 3 to 8.

Start of Treatment (S0)

The output of the treatment high-frequency wave is started.

At the start of the treatment, the resistance component is predominant in the living tissue, so that the living tissue is in a state to be able to be regarded as an electric conductor, and an impedance Z of the living tissue is comparatively low.

Constant-Power Control Step (S1)

The current and voltage values of the treatment high-frequency wave output from the output transformer 34 are detected by the current sensor 43 and the voltage sensor 44, and on the basis of the detected current and voltage values, the treatment high-frequency wave is controlled so that power W of the treatment high-frequency wave output from the output transformer 34 may be constant. A frequency ft of the treatment high-frequency wave is set to a comparatively low frequency fl of, for example, several hundred kHz used in a normal high-frequency treatment apparatus. A high-frequency current flow through the living tissue, and Joule heat is generated in the living tissue. Here, since the impedance Z of the living tissue is comparatively low, and so the high-frequency current is comparatively high, and a calorific value Q1 derived from the Joule heat is proportional to the square of the current, so that comparatively high energy is applied to the living tissue. The provision of the energy to the living tissue causes the breaking of the cell membrane and temperature increases in the extracellular fluid and the intracellular fluid, such that the extracellular fluid and the intracellular fluid are boiled and evaporated, and a vapor layer is generated in the living tissue, and then the impedance Z of the living tissue rapidly increases.

In addition, the frequency ft of the treatment high-frequency wave is not set to a comparatively high frequency fh of, for example, several MHz for the following reason: The impedance based on the inductance component of the cable 36 is schematically in proportion to the frequency, so that if the frequency ft of the treatment high-frequency wave is the comparatively high frequency fh, the impedance based on the inductance component of the cable 36 is comparatively high. On the contrary, the impedance based on the resistance component of the living tissue is comparatively low. As the inductance component of the cable 36 and the resistance component of the living tissue as mentioned above are arranged in series with each other, power consumed in the cable 36 out of the constant power W output from the power supply apparatus 30 increases, and power consumed in the living tissue decreases and the Joule heat generated in the living tissue thus decreases, so that a dehydration effect decreases. On the other hand, the living tissue is in a state to be able to be regarded as an electric conductor, and heat is hardly generated by the high-frequency dielectric heating, so that the dehydration effect attributed to the high-frequency dielectric heating is hardly obtained even if a frequency is set high.

Impedance Measurement Step (S2)

During the constant-power control of the treatment high-frequency wave, the impedance Z of the treatment target living tissue is calculated from the current and voltage values of the treatment high-frequency wave.

Switch Judgment Step (S3)

The control of the treatment high-frequency wave is switched from the constant-power control to constant-voltage control when the impedance Z calculated on the basis of the treatment high-frequency wave has reached the switching threshold value Zc.

Constant-Voltage Control Step (S4)

The capacity component is predominant in the living tissue in which the vapor layer has been generated, and the living tissue is in a state to be able to be regarded as an electric conductor, so that the impedance Z of the living tissue is comparatively high. At the point where the vapor layer is generated in the living tissue and the impedance Z of the living tissue rapidly increases, the extracellular fluid and the intracellular fluid still remain in the living tissue, and the living tissue is not completely dehydrated. However, the impedance Z of the living tissue has increased, so that the high-frequency current flowing through the living tissue decreases, and the calorific value Q1 derived from the Joule heat decreases. In particular, as the impedance based on the capacity component of the cable 36 is schematically in inverse proportion to the frequency of the high-frequency wave, the impedance based on the capacity component of the cable 36 is thus comparatively low. As the capacity component of the cable 36 and the capacity component of the living tissue as mentioned above are arranged in parallel with each other, the high-frequency current flowing through the living tissue further decreases, and the calorific value Q1 derived from the Joule heat further decreases. It is noted that, in order to prevent a discharge from being caused in the electrodes 42, a voltage V of the treatment high-frequency wave needs to be equal to or less than a fixed level, and so there is a limit of the increase of the current flowing through the living tissue by increasing the voltage V. For such reasons, it is difficult to completely dehydrate the living tissue by the Joule heat.

In a constant-voltage control step, the treatment high-frequency wave is controlled so that the voltage V of the treatment high-frequency wave output from the output transformer 34 may be constant. The frequency ft of the treatment high-frequency wave is set to the frequency fh of, for example, several MHz comparatively higher than the frequency used in a normal high-frequency treatment apparatus. The living tissue is in a state to be able to be regarded as an electric conductor, and the living tissue is heated by the high-frequency dielectric heating. A calorific value Q2 derived from the high-frequency dielectric heating is proportional to the square of electric field strength and to frequency, is not affected by the decrease of the current flowing through the living tissue, and is increased by the increase of the frequency. Moreover, the impedance Z of the living tissue is high, so that the influence of the inductance component of the cable 36 is relatively small, and the voltage V applied to the living tissue is sufficiently secured and the electric field strength is also sufficiently secured. Thus, comparatively high energy is applied to the living tissue, and the extracellular fluid and the intracellular fluid remaining in the living tissue can be boiled and evaporated.

Impedance Measurement Step (S5)

During the constant-voltage control of the treatment high-frequency wave, the impedance Z of the treatment target living tissue is calculated from the current and voltage values of the treatment high-frequency wave.

End Judgment Step (S6)

Whether the impedance Z calculated on the basis of the treatment high-frequency wave has reached the end threshold value Ze is judged.

End of Treatment (S7)

The output of the treatment high-frequency wave is stopped.

The high-frequency treatment apparatus and the high-frequency treatment method in the present embodiment have the following advantages.

When the impedance of the living tissue is lower than the switching threshold value Zc, the living tissue is in a state to be able to be regarded as an electric conductor, and a current easily flows through the living tissue, so that the calorific value Q1 derived from the Joule heat proportional to the square of the current is comparatively high. Moreover, the influence of the inductance component of the cable 36 with respect to the resistance component of the living tissue is great, and the ratio of the power consumed in the cable 36 increases, so that the ratio of the power consumed in the living tissue decreases. In such a case, the frequency ft of the treatment high-frequency wave is set to the comparatively low frequency fl of several kHz to reduce the influence of the inductance component of the cable 36, to increase the ratio of the power consumed in the living tissue and to increase the calorific value Q1 derived from the Joule heat, and besides the living tissue is primarily treated by the Joule heat. Thus, a sufficiently high dehydration effect is obtained. On the other hand, when the impedance of the living tissue is higher than the switching threshold value Zc, the living tissue is in a state to be able to be regarded as a dielectric, and the influence of the capacity component of the cable 36 is relatively high, and so it is very difficult for a current to flow through the living tissue. Thus, while the calorific value Q1 derived from the Joule heat proportional to the square of the current is significantly low, the calorific value Q2 derived from the high-frequency dielectric heating is sufficiently high. In such a case, the frequency ft of the treatment high-frequency wave is set to the comparatively high frequency fh of several MHz to increase the calorific value Q2 of the high-frequency dielectric heating proportional to frequency, and besides the living tissue is primarily treated by the high-frequency dielectric heating. Thus, a sufficiently high dehydration effect is obtained. Consequently, it is possible to dehydrate the living tissue surely even when the treatment high-frequency wave is transmitted by the cable 36.

A second embodiment of the present invention is described with reference to FIGS. 10 to 13.

In the present embodiment, a detection high-frequency wave of a comparatively high frequency is used to measure the impedance of the treatment target living tissue.

Figure 10:
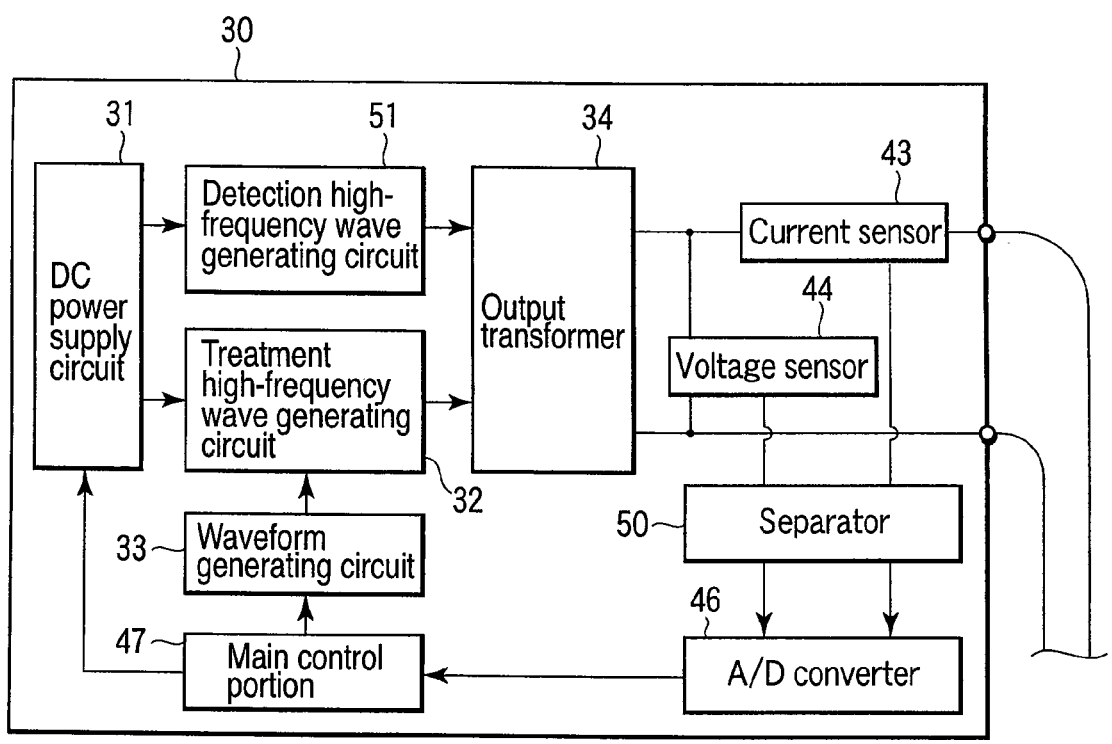
FIG. 10 is a block diagram showing a high-frequency treatment apparatus according to a second embodiment of the present invention.

Referring to FIG. 10, in a power supply apparatus 30, a DC power supply circuit 31 is configured to supply power to a detection high-frequency wave generating circuit 51. The detection high-frequency wave generating circuit 51 is configured to generate the detection high-frequency wave, and to output the detection high-frequency wave to an output transformer 34. Similarly to the treatment high-frequency wave, the detection high-frequency wave is to be supplied from an output transformer 34 to a pair of electrodes 42 via a pair of signal lines 37 of a cable 36, and to be applied to the living tissue held by the pair of electrodes 42. In this way, a detection high-frequency wave output unit is formed by the DC power supply circuit 31, the detection high-frequency wave generating circuit 51 and the output transformer 34. Current and voltage values of the high-frequency wave output from the output transformer 34 are to be detected by a current sensor 43 and a voltage sensor 44, to be separated into a treatment high-frequency wave component and a detection high-frequency wave component by a separator 50, to be A/D-converted by an A/D converter 46, and to be output to a main control portion 47. The main control portion 47 is configured to calculate an impedance of the living tissue on the basis of the current and voltage values of the detection high-frequency wave. As mentioned above, a detection unit in the present embodiment includes the separator 50. The main control portion 47 is configured to control the DC power supply circuit 31 and a waveform generating circuit 33 on the basis of the calculated impedance.

Figure 12:
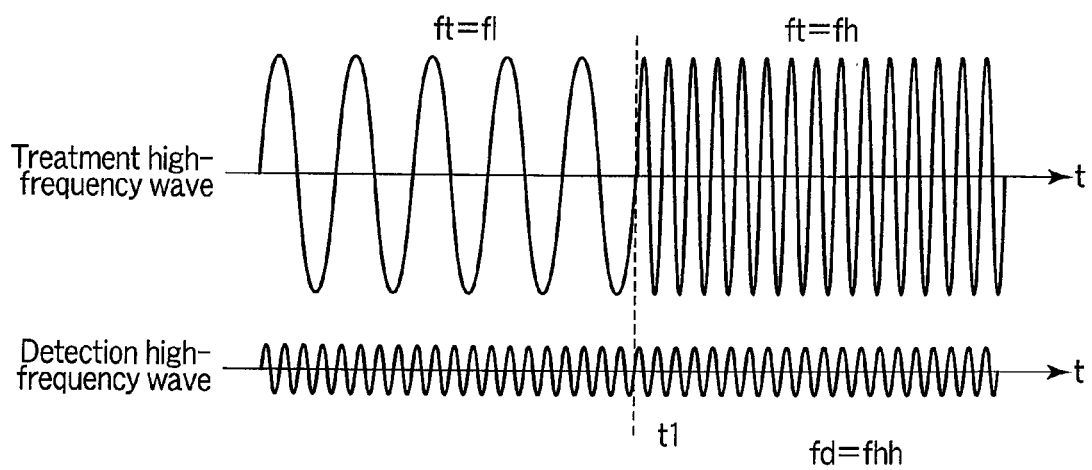
FIG. 12 is a timing chart showing a treatment high-frequency wave and a detection high-frequency wave in the high-frequency treatment method according to the second embodiment of the present invention.

The high-frequency treatment method is described with reference to FIGS. 11 and 12.

Start of Treatment (S0)

The output of the treatment high-frequency wave and the detection high-frequency wave is started.

Constant-Power Control Step (S1)

The constant-power control of the treatment high-frequency wave is performed as in the first embodiment.

Impedance Measurement Step (S2)

During the constant-power control of the treatment high-frequency wave, an impedance Z of the treatment target living tissue is calculated from the current and voltage values of the detection high-frequency wave. A weak voltage sufficiently lower than the voltage of the treatment high-frequency wave is used as the voltage of the detection high-frequency wave. Moreover, a frequency fd of the detection high-frequency wave is maintained to be constant, and is set to a comparatively high frequency fhh of several MHz which is equal to or higher than the comparatively high frequency fh of the treatment high-frequency wave of several MHz. It is noted that, as the comparatively high frequency fhh of several MHz is used as the detection high-frequency wave, an impedance based on the inductance component of the cable 36 is high, and it is necessary to subtract the impedance based on the inductance component of the cable 36 from the impedance directly calculated from the current and voltage values of the detection high-frequency wave in order to calculate the impedance Z of the living tissue. In addition, as the frequency fd of the detection high-frequency wave is maintained to be constant, the impedance based on the inductance component of the cable 36 is also constant.

Switch Judgment Step (S3)

The control of the treatment high-frequency wave is switched from the constant-power control to constant-voltage control when the impedance Z calculated on the basis of the detection high-frequency wave has reached a switching threshold value Zc.

Constant-Voltage Control Step (S4)

The constant-voltage control of the treatment high-frequency wave is performed as in the first embodiment.

Impedance Measurement Step (S5)

During the constant-voltage control of the treatment high-frequency wave, the impedance Z of the treatment target living tissue is calculated from the current and voltage values of the detection high-frequency wave. The frequency fd of the detection high-frequency wave is kept at the comparatively high frequency fhh of several MHz which has been set during the constant-power control of the treatment high-frequency wave.

End Judgment Step (S6)

Whether the impedance Z calculated on the basis of the treatment high-frequency wave has reached an end threshold value Ze is judged.

End of Treatment (S7)

The output of the treatment high-frequency wave and the detection high-frequency wave is stopped.

The high-frequency treatment apparatus and the high-frequency treatment method in the present embodiment have the following advantages.

The impedance of the living tissue has a frequency characteristic, and a measured value of the impedance varies due to a change in the frequency of the high-frequency wave for detecting the impedance. In the present embodiment, the detection high-frequency wave of the constant frequency fhh is used to measure the impedance throughout the treatment of the living tissue, so that it is possible to measure the impedance while excluding the influence of the variation of the measured value of the impedance due to a change in the frequency of the high-frequency wave for detecting the impedance.

Furthermore, the comparatively high frequency fhh of several MHz is used as the frequency fd of the detection high-frequency wave. When the frequency fd of the detection high-frequency wave is high, a impedance based on a capacity component formed from a cell membrane and a vapor layer is measured lower, and the measured impedance is attributed to an impedance mainly based on a resistance component formed from an extracellular fluid and an intracellular fluid. Therefore, even after the vapor layer has started to be generated in the living tissue, it is possible to measure the impedance of the living tissue itself while excluding the influence of the vapor layer.

Figure 13:
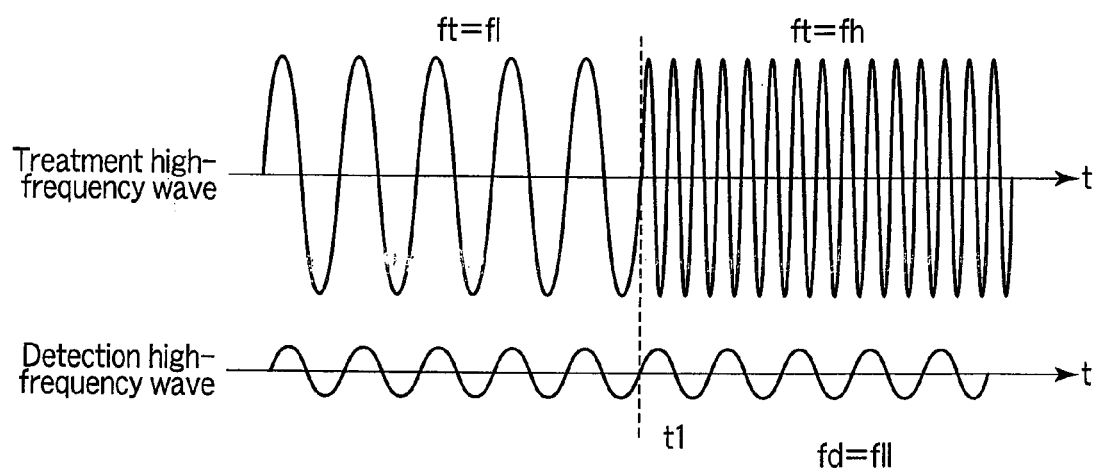
FIG. 13 is a timing chart showing a treatment high-frequency wave and a detection high-frequency wave in a high-frequency treatment method according to a third embodiment of the present invention.

A third embodiment of the present invention is described with reference to FIG. 13.

In the present embodiment, a comparatively low frequency fll of several kHz which is equal to or lower than the comparatively low frequency fl of the treatment high-frequency wave of several kHz is used as a frequency fd of the detection high-frequency wave in contrast to the second embodiment. When the frequency fd of the detection high-frequency wave is low, a impedance based on a capacity component formed from a cell membrane and a vapor layer is measured higher, and the measured impedance is attributed to an impedance mainly based on a capacity component. Therefore, it is possible to detect the breaking of the cell membrane immediately after the start of the provision the treatment high-frequency wave to the living tissue.

Figure 14:
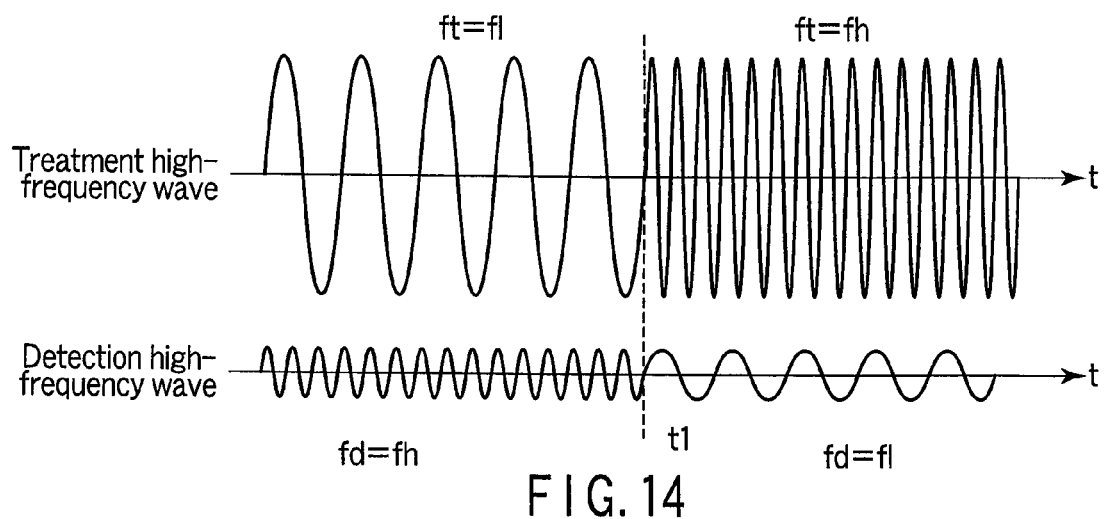
FIG. 14 is a timing chart showing a treatment high-frequency wave and a detection high-frequency wave in a high-frequency treatment method according to a fourth embodiment of the present invention.

A fourth embodiment of the present invention is described with reference to FIG. 14.

In the present embodiment, a main control portion 47 is configured to calculate an impedance of a living tissue on the basis of current and voltage values of a treatment high-frequency wave as in the first embodiment, and also to calculate an impedance of the living tissue on the basis of current and voltage values of a detection high-frequency wave. A frequency different from the frequency ft of the treatment high-frequency wave is used as a frequency fd of the detection high-frequency wave. In the present embodiment, the frequency fd of the detection high-frequency wave is the same as a comparatively high frequency fh of the treatment high-frequency wave of several MHz when a treatment frequency is a comparatively low frequency fl of the treatment high-frequency wave of several kHz, while the frequency fd of the detection high-frequency wave is the same as the comparatively low frequency fl of several kHz when the treatment frequency is the comparatively high frequency fh of several MHz. The main control portion 47 is configured to judge whether the impedance of the living tissue has reached a switching threshold value Zc on the basis of the calculated two impedances.

As described above, the impedance of the living tissue having a frequency characteristic is constantly measured by two high-frequency waves having frequencies different from each other, so that it is possible to accurately detect the state of the living tissue. Particularly, in the present embodiment, the high-frequency wave of the comparatively low frequency fl of several kHz and the high-frequency wave of the comparatively high frequency fh of several MHz are used, thereby enabling the measurement of the impedance of the living tissue itself and the detection of the breaking of a cell membrane as described in the second and third embodiments.

Reference embodiments of the present invention will be described below.

A first reference embodiment of the present invention is described with reference to FIGS. 15A and 15B.

In the present reference embodiment, an edge electrode 52 and a central electrode 53 are used as the electrodes 42 disposed in jaws 41 of a high-frequency accessory 38. When viewed in a direction of contact with the living tissue, the edge electrode 52 is in the shape of a thin frame forming four sides of a rectangle, and the central electrode 53 has a rectangular flat shape and is disposed inside the edge electrode 52. The edge electrode 52 and the central electrode 53 are insulated from each other by an insulating member of a jaw main body. When a coaptation treatment is administered to living tissues, a voltage is applied to a comparatively small region between the pair of edge electrodes 52, and electric field density is higher in this region, so that energy is applied in a concentrated manner, and the dehydration effect is improved. Therefore, the living tissue is uniformly and sufficiently dehydrated regardless of the thickness of the living tissue and the presence of a vapor layer, and uniform and sufficient coaptation strength is obtained. As a result, sufficient coaptation strength is obtained in the edge portions of a coaptation portion, so that the whole coaptation portion is hardly stripped.

A second reference embodiment of the present invention is described with reference to FIG. 16.

In the present embodiment, a plurality of thin rod electrodes 54 are arranged side by side at equal intervals when viewed in a direction of contact with a living tissue. When a coaptation treatment is administered to living tissues, energy is applied in a concentrated manner to each small region between the pair of rod electrodes 54 opposite to each other, so that uniform and sufficient coaptation strength is obtained in each region, and sufficient coaptation strength is obtained in the edge portions of a coaptation portion. Moreover, even if the living tissue has been stripped in a rod-like coaptation portion on one side end, an inner rod-like coaptation portion also has uniform and sufficient coaptation strength and so sufficient coaptation strength is obtained in the edge portion of a new coaptation portion, and the coaptation portion is hardly stripped on the whole.

A third reference embodiment of the present invention is described with reference to FIG. 17.

In the present embodiment, when viewed in a direction of contact with a living tissue, a plurality of thin short rod electrodes 56 are aligned at equal intervals in their longitudinal direction, Lines of the plurality of short rod electrodes 56 are arranged side by side at equal intervals, and the short rod electrodes 56 are alternately arranged in their longitudinal direction between adjacent lines of the short rod electrodes 56. When a coaptation treatment is administered to living tissues, energy is applied in a concentrated manner to each sufficiently small region between the pair of short rod electrodes 56 opposite to each other, so that uniform and sufficient coaptation strength is obtained in each region, and sufficient coaptation strength is obtained in the edge portions of a coaptation portion. Moreover, since undehydrated regions widely remain in the coaptation portion, the regenerative capacity of the living tissue is improved, so that the drop of the coaptation portion is delayed, and the start of the regeneration of the living tissue is promoted.

A fourth reference embodiment of the present invention is described below.

In the present embodiment, treatment high-frequency waves can be separately and independently supplied to the edge electrode 52 and the central electrode 53 in the high-frequency accessory 38 in the first reference embodiment. The treatment high-frequency wave supplied to the edge electrode 52 is to be controlled in the same manner as the treatment high-frequency wave in the first embodiment. That is, a frequency of the treatment high-frequency wave is set to a comparatively low frequency of several hundred kHz until the impedance of the living tissue reaches a switching threshold value Zc, and is set to a comparatively high frequency of several MHz after the switching threshold value Zc has been reached. On the other hand, a frequency of the treatment high-frequency wave supplied to the central electrode 53 is set to a comparatively low frequency of several kHz throughout the coaptation treatment of the living tissue. In the present embodiment, the living tissue between the pair of edge electrodes 52 is dehydrated by Joule heat and high-frequency dielectric heating, so that it is possible to completely dehydrate the living tissue and further increase coaptation strength.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency treatment apparatus comprising:
   a treatment high-frequency wave output unit configured to output a treatment high-frequency wave to be applied to a treatment target living tissue;
   a detection unit configured to detect an impedance of the treatment target living tissue;
   a control unit configured to control the treatment high-frequency wave output unit on the basis of the result of the detection in the detection unit, the control unit configured to set a treatment frequency of the treatment high-frequency wave to a first treatment frequency in order to treat the living tissue primarily by Joule heat when the impedance of the treatment target living tissue is lower than a threshold value and to set the treatment frequency to a second treatment frequency higher than the first treatment frequency in order to treat the living tissue primarily by high-frequency dielectric heating when the impedance of the treatment target living tissue is higher than the threshold value; and
   a detection high-frequency wave output unit configured to output a detection high-frequency wave to be applied to the treatment target living tissue and configured to be controlled by the control unit,
   wherein the detection unit is configured to calculate the impedance of the treatment target living tissue on the basis of the detection high-frequency wave output from the detection high-frequency wave output unit.

2. The high-frequency treatment apparatus according to claim 1, further comprising:
   first and second electrodes configured to apply the treatment high-frequency wave to the treatment target living tissue; and
   a cable configured to transmit the treatment high-frequency wave output from the treatment high-frequency wave output unit to the first and second electrodes and having a induction coefficient and capacity.

3. The high-frequency treatment apparatus according to claim 1, wherein the control unit is configured to set a detection frequency of the detection high-frequency wave to be constant.

4. The high-frequency treatment apparatus according to claim 1, wherein the control unit is configured to set a detection frequency of the detection high-frequency wave to a detection frequency suitable to detect an impedance mainly based on a resistance component of the living tissue.

5. The high-frequency treatment apparatus according to claim 1, wherein the control unit is configured to set a detection frequency of the detection high-frequency wave to a detection frequency suitable to detect an impedance mainly based on a capacity component of the living tissue.

6. The high-frequency treatment apparatus according to claim 1, wherein the control unit is configured to set a detection frequency of the detection high-frequency wave to a detection frequency different from the treatment frequency of the treatment high-frequency wave, and
   the detection unit is configured to calculate the impedance of the treatment target living tissue on the basis of the treatment high-frequency wave.

7. A high-frequency treatment method comprising:
   detecting an impedance of a treatment target living tissue;
   performing a first treatment wherein a treatment high-frequency wave of a first treatment frequency is applied to the living tissue in order to treat the living tissue primarily by Joule heat when the impedance of the treatment target living tissue is lower than a threshold value;
   performing a second treatment wherein a treatment high-frequency wave of a second treatment frequency higher than the first treatment frequency is applied to the living tissue in order to treat the living tissue primarily by high-frequency dielectric heating when the impedance of the treatment target living tissue is higher than the threshold value,
   wherein the detecting includes applying a detection high-frequency wave to the treatment target living tissue and calculating the impedance of the treatment target living tissue on the basis of the detection high-frequency wave applied to the treatment target living tissue.

8. The high-frequency treatment method according to claim 7,
   wherein the performing the first and second treatments includes applying the treatment high-frequency wave to the living tissue via a cable having a induction coefficient and capacity.

9. The high-frequency treatment method according to claim 7, wherein a detection frequency of the detection high-frequency wave is constant.

10. The high-frequency treatment method according to claim 7, wherein a detection frequency of the detection high-frequency wave is a detection frequency suitable to detect the impedance mainly based on a resistance component of the living tissue.

11. The high-frequency treatment method according to claim 7, wherein a detection frequency of the detection high-frequency wave is a detection frequency suitable to detect the impedance mainly based on a capacity component of the living tissue.

12. The high-frequency treatment method according to claim 7, wherein a detection frequency of the detection high-frequency wave is different from the treatment frequency of the treatment high-frequency wave, and
   the detecting further includes calculating the impedance of the treatment target living tissue on the basis of the treatment high-frequency wave.

13. A high-frequency treatment apparatus comprising:
   treatment high-frequency wave output means for outputting a treatment high-frequency wave to be applied to a treatment target living tissue;
   detection means for detecting an impedance of the treatment target living tissue;
   control means for controlling the treatment high-frequency wave output means on the basis of the result of the detection in the detection means, the control means for setting a treatment frequency of the treatment high-frequency wave to a first treatment frequency in order to treat the living tissue primarily by Joule heat when the impedance of the treatment target living tissue is lower than a threshold value and setting the treatment frequency to a second treatment frequency higher than the first treatment frequency in order to treat the living tissue primarily by high-frequency dielectric heating when the impedance of the treatment target living tissue is higher then the threshold value; and a detection high-frequency wave output means configured to output a detection high-frequency wave to be applied to the treatment target living tissue and configured to be controlled by the control means, wherein the detection means is configured to calculate the impedance of the treatment target living tissue on the basis of the detection high-frequency wave output from the detection high-frequency wave output means.

* * * * *